United States Patent
Larin et al.

(10) Patent No.: US 11,406,258 B2
(45) Date of Patent: Aug. 9, 2022

(54) SYSTEM AND METHOD TO MEASURE TISSUE BIOMECHANICAL PROPERTIES WITHOUT EXTERNAL EXCITATION

(71) Applicant: University of Houston System, Houston, TX (US)

(72) Inventors: Kirill V. Larin, Friendswood, TX (US); Achuth Nair, Houston, TX (US); Manmohan Singh, Houston, TX (US); Salavat Aglyamov, Friendswood, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 225 days.

(21) Appl. No.: 16/907,424

(22) Filed: Jun. 22, 2020

(65) Prior Publication Data

US 2020/0329958 A1    Oct. 22, 2020

Related U.S. Application Data (60) Continuation-in-part of application No. 16/558,413, filed on Sep. 3, 2019, which is a division of
(Continued)

(51) Int. Cl.
*A61B 3/00*        (2006.01)
*A61B 3/10*        (2006.01)
(Continued)

(52) U.S. Cl.
CPC .......... *A61B 3/0025* (2013.01); *A61B 3/102* (2013.01); *A61B 3/16* (2013.01); *A61B 3/165* (2013.01);
(Continued)

(58) Field of Classification Search
CPC ......... A61B 3/0025; A61B 3/102; A61B 3/10; A61B 3/16; A61B 3/165; A61B 5/1495;
(Continued)

(56) References Cited

U.S. PATENT DOCUMENTS

| | | |
|---|---|---|
| 2005/0119568 A1 | 6/2005 | Salcudean et al. |
| 2010/0007357 A1 | 1/2010 | Ammari et al. |
| 2014/0323862 A1 | 10/2014 | Silverman et al. |

FOREIGN PATENT DOCUMENTS

| | | |
|---|---|---|
| JP | 2010-125260 | 6/2010 |
| JP | 2010-125260 A | 6/2010 |

(Continued)

OTHER PUBLICATIONS

Nair, et al., "Heartbeat OCE: Corneal Biomechanical Response to Simulated Heartbeat Pulsation Measured by Optical Coherence Elastography", Journal of Biomedical Optics, 2020; 25(5):055001, 10 pages.
(Continued)

*Primary Examiner* — Jack Dinh
(74) *Attorney, Agent, or Firm* — Jackson Walker LLP (57) ABSTRACT

A system and method for measuring biomechanical properties of tissues without external excitation are capable of measuring and quantifying these parameters of tissues in situ and in vivo. The system and method preferably utilize a phase-sensitive optical coherence tomography (OCT) system for measuring the displacement caused by the intrinsic heartbeat. The method allows noninvasive and nondestructive quantification of tissue mechanical properties. Preferably, the method is used to detect tissue stiffness and to evaluate its stiffness due to intrinsic pulsatile motion from the heartbeat. This noninvasive method can evaluate the biomechanical properties of the tissues in vivo for detecting
(Continued)

the onset and progression of degenerative or other diseases and evaluating the efficacy of therapies.

9 Claims, 10 Drawing Sheets

Related U.S. Application Data application No. 15/632,657, filed on Jun. 26, 2017, now Pat. No. 10,405,740, which is a continuation of application No. 14/934,663, filed on Nov. 6, 2015, now Pat. No. 9,687,145.

(60) Provisional application No. 62/171,043, filed on Jun. 4, 2015, provisional application No. 62/077,561, filed on Nov. 10, 2014.

(51) Int. Cl.
*A61B 3/16* (2006.01)
*A61B 5/00* (2006.01)
*A61B 8/10* (2006.01)
*A61B 8/08* (2006.01)

(52) U.S. Cl.
CPC .......... *A61B 5/0051* (2013.01); *A61B 5/0053* (2013.01); *A61B 5/0066* (2013.01); *A61B 5/0093* (2013.01); *A61B 8/10* (2013.01); *A61B 8/485* (2013.01); *A61B 5/0097* (2013.01); *A61B 2576/00* (2013.01)

(58) Field of Classification Search
CPC ....... A61B 5/0073; A61B 5/0066; A61B 5/03; A61B 5/7207; A61B 5/025; A61B 5/0093; A61B 5/14542; A61B 5/7265; A61B 5/0051; A61B 5/0053; A61B 5/25; A61B 5/0097; A61B 8/10; A61B 8/485; A61B 2576/00
See application file for complete search history.

(56) References Cited

FOREIGN PATENT DOCUMENTS

| WO | 2014/138997 | 9/2014 |
|---|---|---|
| WO | 2014-138997 A1 | 9/2014 |
| WO | 2015/168400 | 11/2015 |
| WO | 2015-168400 A1 | 11/2015 |

OTHER PUBLICATIONS

Matveyev, et al., "Vector Method for Strain Estimation in Phase-Sensitive Optical Ccoherence Elastography", Laser Physics Letters, 2018; 15(6):065603, 7 pages.
Pavlatos, et al., "Imaging Corneal Biomechanical Responses to Ocular Pulse Using High-Frequency Ultrasound", IEEE Transactions on Medical Imaging, 2017; 37(2): pp. 663-670.
Clayson, et al., "Ocular Pulse Elastography: Imaging Corneal Biomechanical Responses to Simulated Ocular Pulse Using Ultrasound", Translational Vision Science & Technology, 2020; 9(1):5, pp. 1-11.
International Search Report and Written Opinion dated Feb. 15, 2016 for the corresponding PCT Application No. PCT/US2015/059472.
Han et al., "Air Puff Induced Corneal Vibrations: Theoretical Simulations and Clinical Observations", J Refract Surg., 2014, pp. 208-213, vol. 30, No. 3.
Wollensak et al., "Riboflavin/ultraviolet-a-induced collagen crosslinking for the treatment of keratoconus", American Journal of Ophthalmology, 2003, pp. 620-627, vol. 135, No. 5.
Medeiros et al., "Evaluation of the influence of corneal biomechanical properties on Intraocular pressure measurements using the Ocular Response Analyzer", J. Glaucoma., 2006, pp. 364-370, vol. 15, No. 5.
Hernandez-Andrade et al., "Evaluation of cervical stiffness during pregnancy using semiquantitative ultrasound elastography", Ultrasound. Obstet. Gynecol., 2013, pp. 152-161, vol. 41, No. 2.
Li et al., "Air-pulse OCE for assessment of age-related changes in mouse cornea in vivo", Laser Phys. Lett., 2014, pp. 1-4, vol. 1, No. 6, 065601.
Wang et al., "A focused air-pulse system for optical-coherence-tomography-based measurements of tissue elasticity", Laser Phys. Lett., 2013, pp. 1-6, vol. 10, No. 7, 075605.
Wang et al., "Noncontact measurement of elasticity for the detection of soft-tissue tumors using phase-sensitive optical coherence tomography combined with a focused air-puff system", Opt Lett. 2012, pp. 5184-5186, vol. 37, No. 24.
Tao et al., "Effects of Collagen Cross-Linking on the Interlamellar Cohesive Strength of Porcine Cornea," Cornea, 2013, pp. 169-173, vol. 32, No. 2.
Twa et al., "Spatial characterization of corneal biomechanical properties with optical coherence elastography after UV cross-linking," Biomedical Optics Express, 2014, pp. 1419-1427, vol. 5, No. 5.
Kotecha et al., "Biomechanical parameters of the cornea measured with the Ocular Response Analyzer in normal eyes," BMC Ophthalmology, 2014, pp. 1-7, vol. 14, Issue, 1, No. 11.
Charman, "The eye in focus: accommodation and presbyopia," Clinical and Experimental Optometry, 2008, pp. 207-225, vol. 91, No. 3.
Glasser et al., "Presbyopia and the optical changes in the human crystalline lens with age," Vision Res., 1998, pp. 209-229, vol. 38, No. 2.
Glasser et al., "Aging of the human crystalline lens and presbyopia," Int. Ophthalmol. Clin., 2001, pp. 1-15, vol. 41.
Heys et al., "Massive increase in the stiffness of the human lens nucleus with age: the basis for presbyopia?" Molecular Vision, 2004, pp. 956-963, vol. 10.
Yoon et al., "The mechanical properties of ex vivo bovine and porcine crystalline lenses: age-related changes and location-dependent variations," Ultrasound Med. Biol., 2013, pp. 1120-1127 vol. 39, No. 6.
Reilly et al., "Microindentation of the young porcine ocular lens," Journal of Biomechanical Engineering, 2009, pp. 044502-1-044504, vol. 131.
Erpelding et al., "Mapping age-related elasticity changes in porcine lenses using bubble-based acoustic radiation force," Exp Eye Res., 2007, pp. 332-341, vol. 84, No. 2.
Hollman et al., "Mapping elasticity in human lenses using bubble-based acoustic radiation force," Exp Eye Res., 2007, pp. 890-893, vol. 85, No. 6.
Glasser, "Restoration of accommodation: surgical options for correction of presbyopia," Clin Exp Optom, 2008, pp. 279-295, vol. 91, No. 3.
Schumacher et al., "Femtosecond laser induced flexibility change of human donor lenses," Vision Research, 2009, pp. 1853-1859, vol. 49.
Sarvazyan et al., "An overview of elastography—an emerging branch of medical imaging," Curr. Med. Imaging Rev.. 2011, pp. 255-282, vol. 7, No. 4.
Kennedy et al., "In vivo three-dimensional optical coherence elastography," Opt Express, 2011, pp. 6623-6634, vol. 19, No. 7.
Yoon et al., "High pulse repetition frequency ultrasound system for the ex vivo measurement of mechanical properties of crystalline lenses with laser-induced microbubbles interrogated by acoustic radiation force," Phys Med Biol., 2012, pp. 4871-4884, vol. 57, No. 15.
Scarcelli et al., "In vivo Brillouin optical microscopy of the human eye," Opt Express, 2012, pp. 9197-9202, vol. 20, No. 8.
Scarcelli et al., "In vivo measurement of age-related stiffening in the crystalline lens by Brillouin optical microscopy," Biophys J., 2011, pp. 1539-1545, vol. 101, No. 6.

(56) References Cited

OTHER PUBLICATIONS

Bailey et al., "Light-scattering study of the normal human eye lens: elastic properties and age dependence," IEEE T Bio-Med. Eng., 2010, pp. 2910-2917, vol. 57, No. 12.
Reiß et al. "Spatially resolved Brillouin spectroscopy to determine the rheological properties of the eye lens," Biomed Opt Express, 2011, pp. 2144-2159, vol. 2, No. 8.
Qi et al., "Phase-resolved acoustic radiation force optical coherence elastography," J. Biomed Opt., 2012, pp. 1-3, vol. 17, No. 11.
Wang et al., "Phase-sensitive optical coherence elastography for mapping tissue microstrains in real time," Appl Phys Lett., 2007, vol. 90, No. 16, 164105.
Sun et al., "Optical coherence elastography: current status and future applications," J Biomed Opt., 2011, pp. 1-12, vol. 16, No. 4.
Liang et al., "Optical micro-scale mapping of dynamic biomechanical tissue properties," Opt. Express, 2008, pp. 11052-11065, vol. 16, No. 5.
Kennedy et al., "Optical palpation: optical coherence tomography-based tactile imaging using a compliant sensor," Opt Lett., 2014, pp. 3014-3017, vol. 39, No. 10.
Rogowska et al., "Optical coherence tomographic elastography technique for measuring deformation and strain of atherosclerotic tissues," Heart, 2004, pp. 556-562, vol. 90.
Wang et al., "Shear wave imaging optical coherence tomography (SWI-OCT) for ocular tissue biomechanics," Opt Lett., 2014, pp. 41-44, vol. 39, No. 1.
Wang et al. "Detection and monitoring of microparticles under skin by optical coherence tomography as an approach to continuous glucose sensing using implanted retroreflectors," IEEE Sens J., 2013, pp. 4534-4541, vol. 13, No. 11.
Aglyamov et al., "Model-based optical coherence elastography using acoustic radiation force," Proc. SPIE, vol. 8946, Optical Elastography and Tissue Biomechanics, 2014, 89460T.
Aglyamov et al., "Model-based reconstructive elasticity imaging using ultrasound," Int. J. Biomed. Imaging, 2007, pp. 1-11, vol. 2007, ID, 35830.
Ziebarth et al., "Atomic force microscopy measurements of lens elasticity in monkey eyes," Molecular Vision. 2007, pp. 504-510, vol. 13.
Wang et al., "Assessing the mechanical properties of tissue-mimicking phantoms at different depths as an approach to measure biomechanical gradient of crystalline lens," Biomed Opt Express, 2013, pp. 2769-2780, vol. 4, No. 12.
Ruberti et al., "Corneal Biomechanics and Biomaterials", Annual review of biomedical engineering, 2011, pp. 269-295, vol. 13.
Li et al., "Dynamic OCE measurement of the biomechanical properties of gelatin phantom and mouse cornea in vivo", Proc. of SPIE, 2013, pp. (85711 T-1)-(85711T-8), vol. 8571, Optical Coherence Tomography and Coherence Domain Optical Methods in Biomedicine XVII.
Liu et al., "Corneal Stiffness Affects IOP Elevation during Rapid Volume Change in the Eye", Investigative ophthalmology & visual science, 2009, pp. 2224-2229, vol. 50, No. 5.
Kennedy et al., "A Review of Optical Coherence Elastography: Fundamentals, Techniques and Prospects", IEEE Journal of Selected Topics in Quantum Electronics, 2014, vol. 20, No. 2.
Venkatesh et al., "Magnetic Resonance Elastography of Liver: Technique, Analysis, and Clinical Applications", Journal of Magnetic Resonance imaging, 2013, pp. 544-555, vol. 37, No. 3.
Liang et al., "Biomechanical Properties of In Vivo Human Skin From Dynamic Optical Coherence Elastography", IEEE Trans Biomed Eng., 2010, pp. 953-959, vol. 57, No. 4.
Li et al., "Quantitative elastography provided by surface acoustic waves measured by phase-sensitive optical coherence tomography", Optics Letters, 2012, pp. 722-724, vol. 37, No. 4.
Doyle, "Wave Propagation in Structures: Spectral Analysis Using Fast Discrete Fourier Transform", 1997, pp. 198-274, 2nd edition, Springer-Verlag, New York (1997).
Singh et al., "Study of gelatin-agar intermolecular aggregates in the supernatant of its coacervate," Colloids and surfaces B: Biointerfaces, 2007, pp. 29-36, vol. 57, No. 1.
Pau, et al., "The increasing sclerosis of the human lens with age and its relevance to accommodation and presbyopia", Graefe's Arch Clin Exp Ophthalmol, 1991, pp. 294-296, vol. 229.
Ripken et al., "fs-Laser induced elasticity changes to improve presbyopic lens accommodation", Graefes Arch Clin Exp Ophthalmol, 2008, pp. 897-906, vol. 246, Springer.
Mello et al., "Femtosecond laser photodisruption of the crystalline lens for restoring accommodation", International Ophthalmology Clinics, 2011, pp. 87-95, vol. 51, No. 2.
Sinkus et al., "Elasticity Imaging via MRI: Basics, Overcoming the waveguide limit, and clinical liver results", Cirrent Medical Imaging Reviews, 2012, pp. 56-63, vol. 8.
Garra, "Imaging and Estimation of Tissue Elasticity by Ultrasound", Ultrasound Quarterly, Review Article: CME Article, 2007, pp. 255-268, vol. 23, No. 4.
Kennedy et al., "Analysis of mechanical contrast in optical coherence elastography", Journal of Biomedical Optics, 2013, pp. (121508-1)-(121508-12), vol. 18, No. 12.
Qi et al., "Confocal acoustic radiation force optical coherence elastography using a ring ultrasonic transducer", Applied Physics Letters, 2014, pp. (123702-1)-(123702-4), vol. 104.
Razani et al., "Optical coherence tomography detection of shear wave propagation in inhomogeneous tissue equivalent phantoms and ex-vivo carotid artery samples", Biomedical Optics Express, 2014, pp. 895-906, vol. 5, No. 3.
Aglyamov, et al. "Assessment of the depth-dependence of the mechanical parameters of a layered medium using surface excitation and motion measurements on the surface", Ultrasonics Symposium (IUS), 2013 IEEE International, 2013, pp. 1252-1255.
Duck, "Medical and non-medical protection standards for ultrasound and infrasound", Progress in Biophysics and Molecular Biology, 2007, pp. 176-191, vol. 93.
Muthupillai et al., "Magnetic-resonance elastography by direct visualization of propagating acoustic strain waves", Science, 1995, pp. 1854-1857, vol. 269, No. 5232.
Lubatschowski et al., "Femtosecond lentotomy: generating gliding planes inside the crystalline lens to regain accommodation ability", J. Biophotonics, 2010, pp. 265-268, vol. 3, No. 5-6.
Ruberti et al., "Corneal Biomechanics and Biomaterials", Annual review of biomedical engineering, 2011, pp. 269-295, vol. 13.
Keennedy et al., "A Review of Optical Coherence Elastography: Fundamentals, Techniques and Prospects", IEEE Journal of Selected Topics in Quantum Electronics, 2014, vol. 20, No. 2.
The International Search Report and the Written Opinion dated Feb. 15, 2016 for the corresponding PCT application No. PCT/US2015/059472.
Han et al., "Air Puff Induced Corneal Vibrations: Theoretical Simulations and Clinical Observations," J Refract Surg., 2014, pp. 208-213, vol. 30, No. 3.
Li et al., "Air-pulse OCE for assessment of age-related changes in mouse cornea in vivo," Laser Phys. Lett., 2014, pp. 1-4, vol. No. 6, 065601.
Baily et al., "Light-scattering study of the normal human eye lens: elastic properties and age dependence," IEEE T Bio-Med. Eng., 2010, pp. 2910-2917, vol. 57, No. 12.

SYSTEM AND METHOD TO MEASURE TISSUE BIOMECHANICAL PROPERTIES WITHOUT EXTERNAL EXCITATION

This application is a continuation-in-part of and claims priority to U.S. patent application Ser. No. 16/558,413, filed Sep. 3, 2019, entitled "Optical Coherence Elastography to Assess Biomechanics and Detect Progression of Ocular and Other Tissues Degenerative Diseases," which is a divisional of and claims priority to U.S. patent application Ser. No. 15/632,657, filed Jun. 26, 2017, entitled "Optical Coherence Elastography to Assess Biomechanics and Detect Progression of Ocular and Other Tissues Degenerative Diseases," which is a continuation application of and claims priority to U.S. patent application Ser. No. 14/934,663, filed Nov. 6, 2015, entitled "Optical Coherence Elastography to Assess Biomechanics and Detect Progression of Ocular and Other Tissues Degenerative Diseases," which claims priority to U.S. Provisional Patent Application Ser. No. 62/077,561, filed Nov. 10, 2014, entitled "Optical Coherence Elastography to Detect the Onset and Progression of Corneal Degenerative Diseases," and U.S. Provisional Patent Application Ser. No. 62/171,043, filed Jun. 4, 2015, entitled "Ultrasound and Optical Coherence Elastography to Assess Biomechanics of Ocular and Other Tissues," and the entire contents of these applications are hereby incorporated by reference.

The present invention used in part funds from the National Institute of Health (NIH), No. R01EY022362. The United States Government has certain rights in the invention.

BACKGROUND

This disclosure pertains to a method for assessing the biomechanical properties of the cornea and other tissues and for detecting and differentiating tissue stiffness without the need for any external excitation. The pulsatile motion within the body, e.g., from the heartbeat, creates small displacements, which are detected by a system.

Changes in the viscoelastic properties of tissues are associated with the onset and progression of different diseases as well as changes due to therapeutic procedures. Therefore, it is essential to assess and quantify tissue mechanical properties for disease detection, during disease progression, and for evaluation of different therapeutic procedures.

For example, keratoconus is associated with localized reduced rigidity of the cornea, and the information regarding corneal stiffness is useful to provide improved diagnosis and monitoring of this pathological status. Also, real-time in vivo measurement of the spatial elasticity distribution with microscopic scale in the cornea could lead to adaptive mechanical modeling of the individual corneal structure which is extremely important to prevent over-corrections, under-corrections, and ectasia from refractive surgeries, such as LASIK, and to further optimize surgical procedures.

Structurally degenerative diseases such as keratoconus can significantly alter the stiffness of the cornea, directly affecting the quality of vision. Keratoconus can pathologically decrease the localized stiffness of the cornea, leading to a loss in the quality of vision. Detecting changes in the biomechanical properties of ocular tissues, such as stiffness of the cornea, can aid in the diagnosis of these structurally degenerative diseases.

UV-induced collagen cross-linking (CXL) is an emerging treatment that effectively increases corneal stiffness and is applied clinically to treat keratoconus. The effectiveness of this treatment may be analyzed and improved by measuring the corneal stiffness both before and after treatment.

In addition, cardiovascular and cerebrovascular diseases and associated ischemic events can be caused by changes in vasculature stiffness. Hardening of the vessel wall increases blood pressure because the vessels are less compliant, and therefore, cannot accommodate during the pulsatile activity during blood pulsation. Therefore, measuring the stiffness of the vasculature can provide critical information for cardiovascular health.

Elastography is an emerging technique that can map the local mechanical properties of tissues. Ultrasound elastography (USE) and magnetic resonance elastography (MRE) have experienced rapid development during the past couple of decades as clinical diagnostic tools. One common principle of these techniques is correlating tissue deformation caused by the external mechanical excitation to tissue elasticity. However, these techniques' use of external excitation limits evaluation of the tissue mechanical properties due to various factors such as excitation bandwidth, tissue response, and patient comfort. The basic feasibility of using Brillouin microscopy to measure the cornea elasticity both in vitro and in vivo has been explored. Brillouin microscopy can be implemented using simple instrumentation, but it has a relatively slow acquisition time. There is also uncertainty on how to correlate Brillouin shift (modulus) to the classical mechanical description of tissues (e.g. Young modulus). Other nano-scale elastography techniques, such as atomic force microscopy, require lengthy acquisition times and contact with the tissue.

What is needed, therefore, is an improved, noninvasive and highly sensitive method to assess the mechanical properties of the ocular and other tissues with high resolution and sensitivity, preferably without contact with the tissue.

Moreover, measuring the stiffness of the cornea, or other ocular tissues, without any external excitation, would further improve the capability for ocular tissue assessment by ensuring there are no issues with patient discomfort and for even more rapid imaging.

SUMMARY

The present disclosure relates generally to methods and systems for assessing the biomechanical properties of tissues non-invasively, to a method using, for example, optical coherence elastography (OCE), for detecting tissue stiffness, such as stiffness of the cornea, sclera, skin, blood vessels, and the like. The methods described herein for biomechanical tissue quantification are demonstrated in the case of the cornea but are generally applicable for all soft and hard tissues in the body.

Optical coherence elastography (OCE) is capable of direct and high-resolution assessment of mechanical properties of tissue and, therefore, overcomes the limitations of previously-used techniques. OCE generally employs high-resolution optical coherence tomography (OCT) to detect the sample deformation induced by an external force. In comparison to ultrasound elastography (USE) and magnetic resonance elastography (MRE), OCE can provide superior spatial imaging resolution, faster acquisition speed, and greater displacement sensitivity.

In one aspect, this disclosure relates to a method for quantifying biomechanical properties of a tissue, comprising: using optical coherence tomography (OCT) or any other low-coherence interferometry and/or phase-sensitive subsystem to image a tissue sample and measure intrinsic displacements, generally produced by the pulsatile motion from the cardiovascular system; and quantifying the biomechanical properties of the tissue based on the analysis of the displacement. The step of quantifying may use an algorithm.

The present system utilizes a phase-sensitive OCT system for measuring the tissue displacement caused by the intrinsic pulses from the pulsatile forces of the cardiovascular system. The system allows for a noninvasive and highly sensitive method to assess the mechanical properties of the tissue in vivo.

The present method compares the displacement amplitude induced by the pulsatile forces from the cardiovascular system. The amplitude of the displacement is mapped and compared at different states during the pulsatile motion. This noninvasive method has the potential to detect the early stages of ocular diseases such as keratoconus or to be applied during cross-linking (CXL) procedures for therapy evaluation and personalization.

BRIEF DESCRIPTION OF THE DRAWINGS

FIGS. 8 (a) and (b) show sample displacement frames and corresponding voltage from a chest-mounted pressure transducer during in vivo imaging of an anesthetized rabbit. The cornea was compressed against a glass slide for stabilization. The frame time is indicated by the vertical line in the transducer voltage plot in the bottom sub-figure.

FIG. 8 (c) shows a profile of the average corneal strain plotted alongside the voltage of the chest-mounted pressure transducer showing that the present method can measure the pulsatile motion in the cornea due to the heartbeat in vivo.

DETAILED DESCRIPTION OF PREFERRED EMBODIMENTS

The present disclosure relates to methods utilizing optical coherence elastography (OCE) to detect tissue stiffness with no external excitation. Previous studies have demonstrated that OCE is feasible for quantitatively assessing the elasticity of a sample but required external excitation. Preferably, the method is used to quantify corneal biomechanical properties. The present method uses phase-sensitive OCT and can distinguish untreated (UT) and riboflavin/UV crosslinked (CXL) corneas due to differences in stiffness and differences in stiffness due to different baseline intraocular pressures. The method can further differentiate UT and CXL regions in a partially crosslinked cornea. This noninvasive method can evaluate the biomechanical properties of the cornea in vivo for detecting the onset and progression of corneal degenerative diseases such as keratoconus and for evaluating the efficacy of therapies such as CXL.

Figure 1:
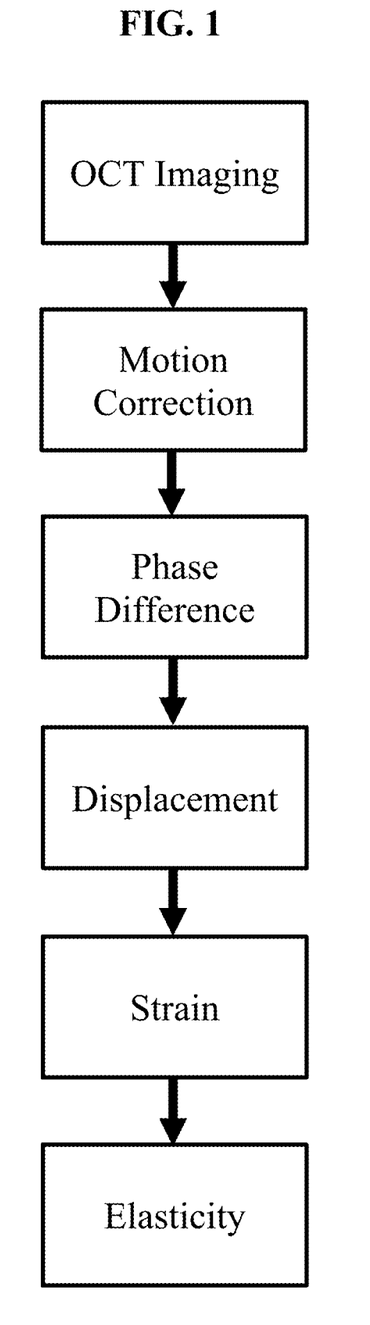
FIG. 1 shows a flow chart describing an exemplary method for imaging pulsatile motion in tissue, such as the cornea, induced by an intrinsic pulse, such as a heartbeat, during imaging, and quantifying tissue biomechanical properties.

FIG. 1 shows a flow chart illustrating an example of a method encompassed by the present disclosure. The sample can be stabilized and is imaged rapidly by the phase-sensitive optical coherence elastography (PhS-OCE) system. An electrocardiogram can be measured for corroborating the OCE-measured data with the heartbeat. The phase difference is calculated from successive OCT frames after motion correction, which is then translated to displacement. Since the structural image is also obtained, the strain is then mapped on to the cornea. Either with or without external IOP measurement, the strain can then be converted to elasticity.

Generally, the present method is for measuring or assessing tissue biomechanical properties (e.g. stiffness and viscosity) with no external excitation. In an exemplary embodiment, a first step is imaging the tissue sample at one or more regions of the tissue sample using phase sensitive and sufficiently high speed interferometry (low-coherence interferometry or optical coherence tomography, which is preferred). The sample may be imaged in either 2D (axial and transverse), 3D (axial and both transverse dimensions), or 4D (axial, both transverse axes, and time). Motion in the sample is detected between successive images of the sample, where at least part of that motion is generated as a result of an internal or intrinsic force, such as the pulsatile motion from the cardiovascular system. The next step is correcting the detected motion due to sources not of interest, or any source that is not the internal or intrinsic force. Motion correction can be accomplished by various methods, such as image registration, cross-correlation, or spatio-temporal filtering. This generates detected intrinsic motion in various successive images of the sample that is due primarily to the internal or intrinsic force. A next step is determining motion information between images of the tissue sample that show detected intrinsic motion. The motion information can be the optical phase difference between successive frames or with reference to a specific frame of the images of the sample in which the intrinsic motion has been detected. For example, a selected frame (x,z) of complex data is multiplied with complex conjugate of the successive complex data frame after the previously mentioned motion correction. The angle of resulting complex data frame is the optical phase difference. The next step is to translate the motion information in the images to displacement of the tissue sample over time. The step of calculating displacement based on detected phase different information may be by phase-sensitive measurements, speckle tracking, motion tracking, or digital correlation methods, and the displacement can be in any direction. For example, the phase difference, $\Delta\varphi$ can be directly translated to displacement, $\Delta d$ by $$\Delta d = \frac{\Delta\varphi\lambda_0}{4\pi n}$$

where $\lambda_0$ is the central wavelength of the imaging system and n is the refractive index of the sample at the central wavelength of the imaging system. Spatio-temporal smoothing or averaging can be applied at any step to reduce noise.

A next preferred step is to use the displacement of the tissue sample to calculate strain. The strain, $\in$ can be calculated by least-squares linear fitting the measured displacement, $\Delta d$, over a region of interest, $\Delta z$, along a selected axis of deformation by $$\epsilon = \frac{\Delta d}{\Delta z}.$$

A next preferred step is to use the calculated strain to calculate elasticity of the tissue sample either with or without external measurement of the baseline or dynamic pressure. For example, in the cornea, the intraocular pressure can be assumed as the applied pressure so the elasticity, E, by $$E = \frac{IOP}{\epsilon}.$$

In addition a pre-calibrated stress sensor could be utilized, which could map the applied stress, $\alpha$, to the sample to calculate the elasticity by $$E = \frac{\sigma}{\epsilon}.$$

Different calculated properties, such as displacement, strain and elasticity, may be attributed to different regions of the tissue sample based on the imaging. The region exhibiting lesser stiffness/elasticity and greater displacement/strain is softer, and the region exhibiting greater stiffness/elasticity and lesser displacement/strain is stiffer. The step of determining or calculating biomechanical properties of the tissue may be considered the step of calculating one or more of displacement, strain, bulk modulus, and/or Young's modulus using the optical phase difference information that is detected or determined from images of the tissue sample.

In preferred embodiments, the tissue samples are ocular tissue samples. The pressure measured is the eye-globe intraocular pressure.

An example demonstrated herein is a porcine cornea in the whole eye-globe configuration with an artificially controlled pressure to simulate the heartbeat.

Figure 2:
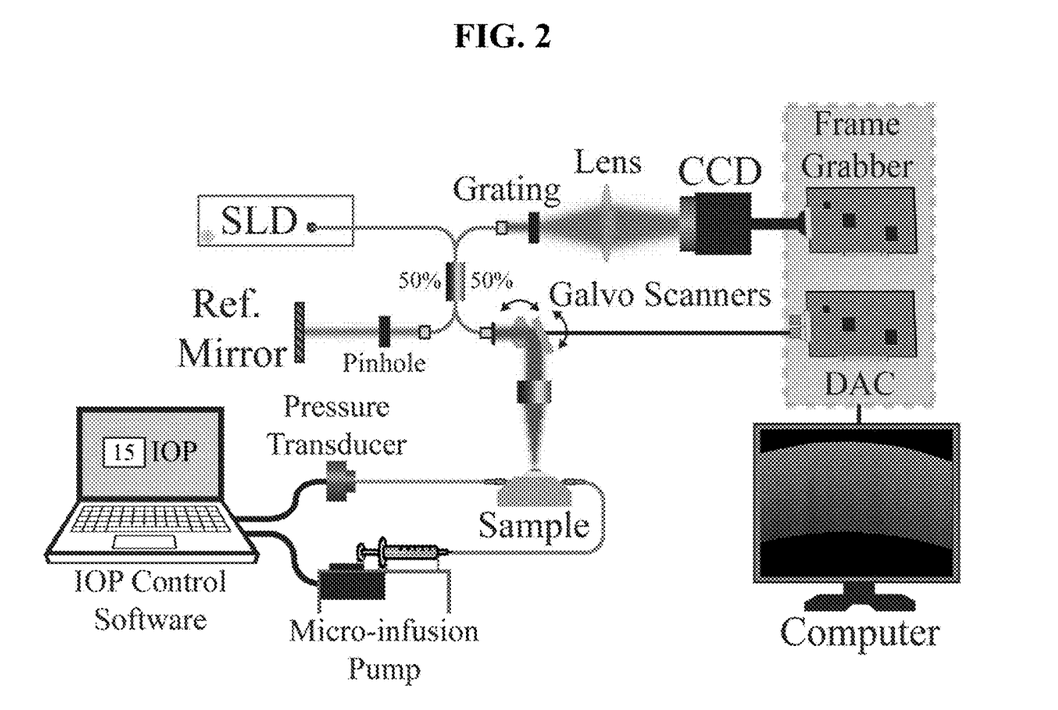
FIG. 2 shows a schematic of an exemplary phase-sensitive optical coherence elastography (OCE) system for measuring corneal displacement due to a simulated ocular pulse in an in situ cornea sample in the whole eye-globe configuration. CCD: charged coupled device, DAC: digital to analog converter, IOP: intraocular pressure, SLD: superluminescent diode.

The exemplary OCE system is phase-sensitive. The OCE system is preferably used in conjunction with a data analyzing algorithm. Based on measurements from the OCE system, the data analyzing algorithm can quantify the mechanical parameters of the cornea. Any suitable computer or data processor programmed with the data analyzing algorithm can be used to make these calculations. The mechanical parameters include parameters such as displacement amplitude, strain, bulk modulus, elasticity, stiffness, and/or Young's modulus. In preferred embodiments, the data analyzing algorithm comprises the steps of correcting the bulk motion of the sample, calculating the phase difference, calculating the displacement, calculating the strain, mapping an applied stress, and calculating the elasticity of the sample. A preferred example of a data analyzing algorithm that may be useful in the current system and method is shown in FIG. 2. These calculations are performed for each step in time and can be correlated to time-matched physiological measurements, such as by an electrocardiogram, pressure transducer, or pulse oximeter.

FIG. 2 shows a schematic of an example of a phase-sensitive OCE system. The setup consists of an optical coherence tomography (OCT) imaging system and an artificial intraocular pressure (IOP) control system for validation testing. The OCT system is based on a Michelson interferomter and a superluminescent diode (SLD). The light from the SLD is fed to a 50/50 fiber optic coupler. The light is them split into two arms. One arm is the sample arm, which is focused on the sample with an objective lens. The beam is scanned across the sample by a pair of mirror-mounted galvanometer mirrors that are controlled by software driving a digital-to-analog converter (DAC). The back scattered light from the sample arm is then collected and combined with the reflected light from the reference arm, which has a mirror. Here the interference pattern is then spread by an optical grating and focused onto a charge-coupled device (CDD) line scan camera. A frame grabber in the computer captures the data from the camera for processing. The intraocular pressure (IOP) is controlled by a closed-loop feedback system. The closed loop is comprised of a pressure transducer and a micro-infusion pump which are controlled by custom software.

For experimental validation, the biomechanical properties of in situ porcine corneas were analyzed using a phase-sensitive OCE system. Experiments were performed on the corneas of pigs in situ (intact eye-globe). The intraocular pressure (IOP) inside the eye-globe was artificially modulated.

Experimental validation was also performed on anesthetized rabbits in vivo. The OCE system and accompanying data analysis algorithm was demonstrated as a promising tool for noninvasive assessment of the changes in the corneal biomechanical properties due to various physiological conditions and treatments. The high displacement sensitivity of phase-sensitive OCT detection enables the measurement of sub-micron displacements throughout the cornea, which is critical for in vivo study as the pulsatile motion is very small and undetectable by other means. In addition, the high spatial resolution of OCT allows a highly-localized investigation of the mechanical properties of the cornea.

Example 1. In Situ Measurement and Validation

A phase-sensitive OCE system was utilized, which consisted of a phase-sensitive spectral domain OCT system. The OCT system was comprised of a superluminescent diode with central wavelength of 840 nm, bandwidth of ~50 nm, and output power of ~12 mW. The axial resolution of the system was ~6 μm in air. The experimentally measured displacement stability of the system was ~5 nm in air.

A validation study was initially conducted on in situ porcine corneas in the whole eye-globe configuration. The eye-globes were placed in a holder and cannulated with two needles. One needle was used for fluid infusion and withdrawal, and the other needle was used for pressure sensing for closed-loop feedback. The IOP was then fluctuated in a sinusoidal pattern to simulate the intrinsic pulsatile motion induced by the heartbeat. Repeated OCT images were acquired at the same location for a period of a several seconds. After measurements on the corneas, they were then cross-linked by the standard riboflavin/UV "Dresden" corneal collagen crosslinking (CXL) protocol. The OCE measurements were then repeated.

Figure 3:
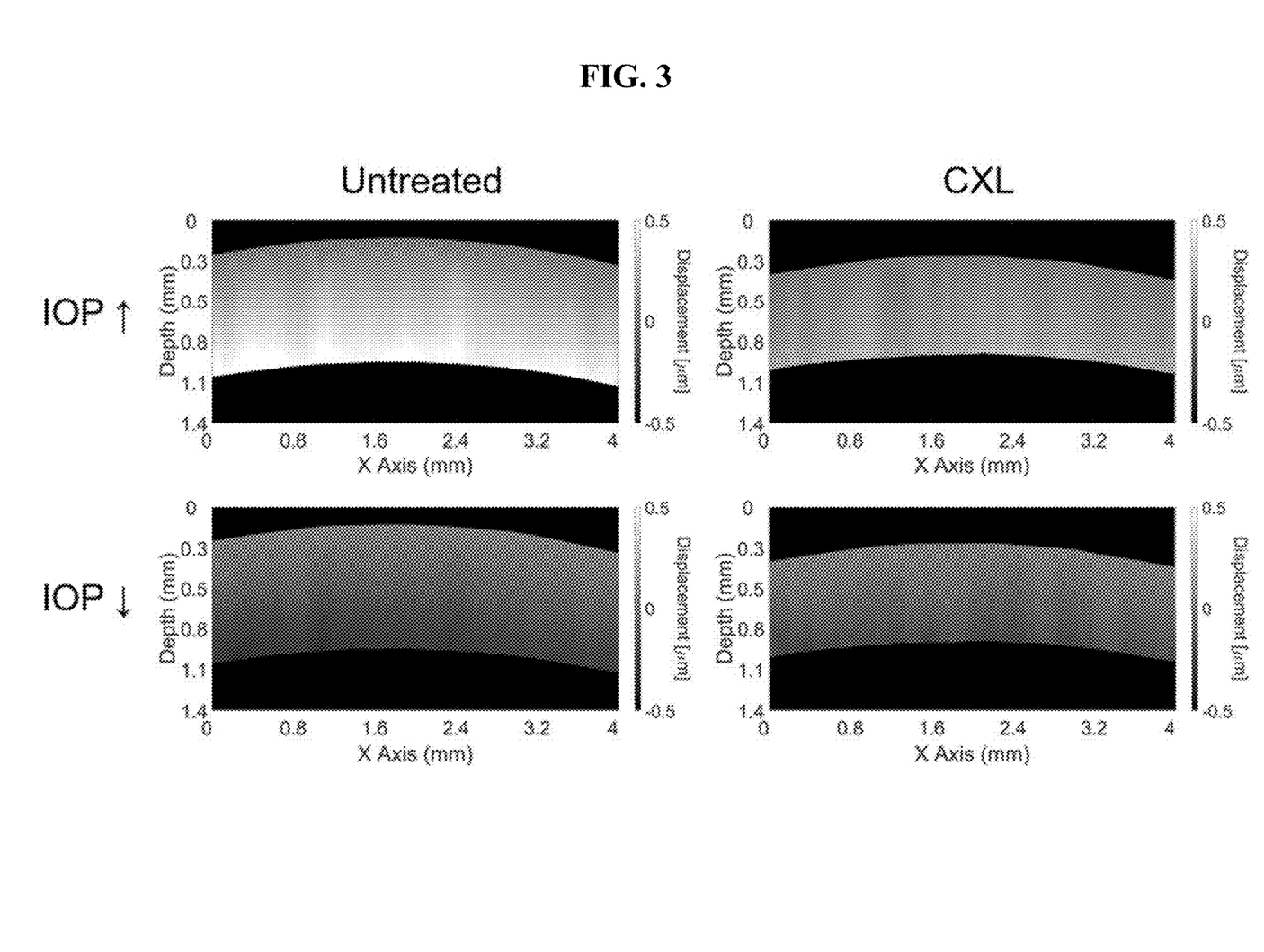
FIG. 3 shows (top left) instantaneous displacement in an untreated in situ porcine cornea, where the fluid is infused into the eye-globe to simulate one phase of the pulsatile motion in the cornea; (bottom left) instantaneous displacement in an untreated in situ porcine cornea where fluid is withdrawn from the eye-globe to simulate one phase of the pulsatile motion in the cornea; (top right) instantaneous displacement in an UV/riboflavin crosslinked in situ porcine cornea where fluid is infused into the eye-globe to simulate one phase of the pulsatile motion in the cornea, (bottom right) instantaneous displacement in an UV/riboflavin crosslinked in situ porcine cornea where fluid is withdrawn from the eye-globe to simulate one phase of the pulsatile motion in the cornea.

As shown in FIG. 3, there was a displacement in cornea in the upwards direction (i.e., compression of the tissue) when the fluid was infused into the eye-globe (top row). As fluid was withdrawn from the eye-globe (bottom row), the displacement was in the downwards direction (i.e., expansion in the tissue). Since the data was normalized to the surface, upwards displacement indicates compression, and downwards displacement indicates extension. The amplitude of the displacement was greater in the untreated corneas (left column) as compared to the crosslinked (CXL) corneas (right column) indicating an increase in stiffness after CXL.

Figure 4:
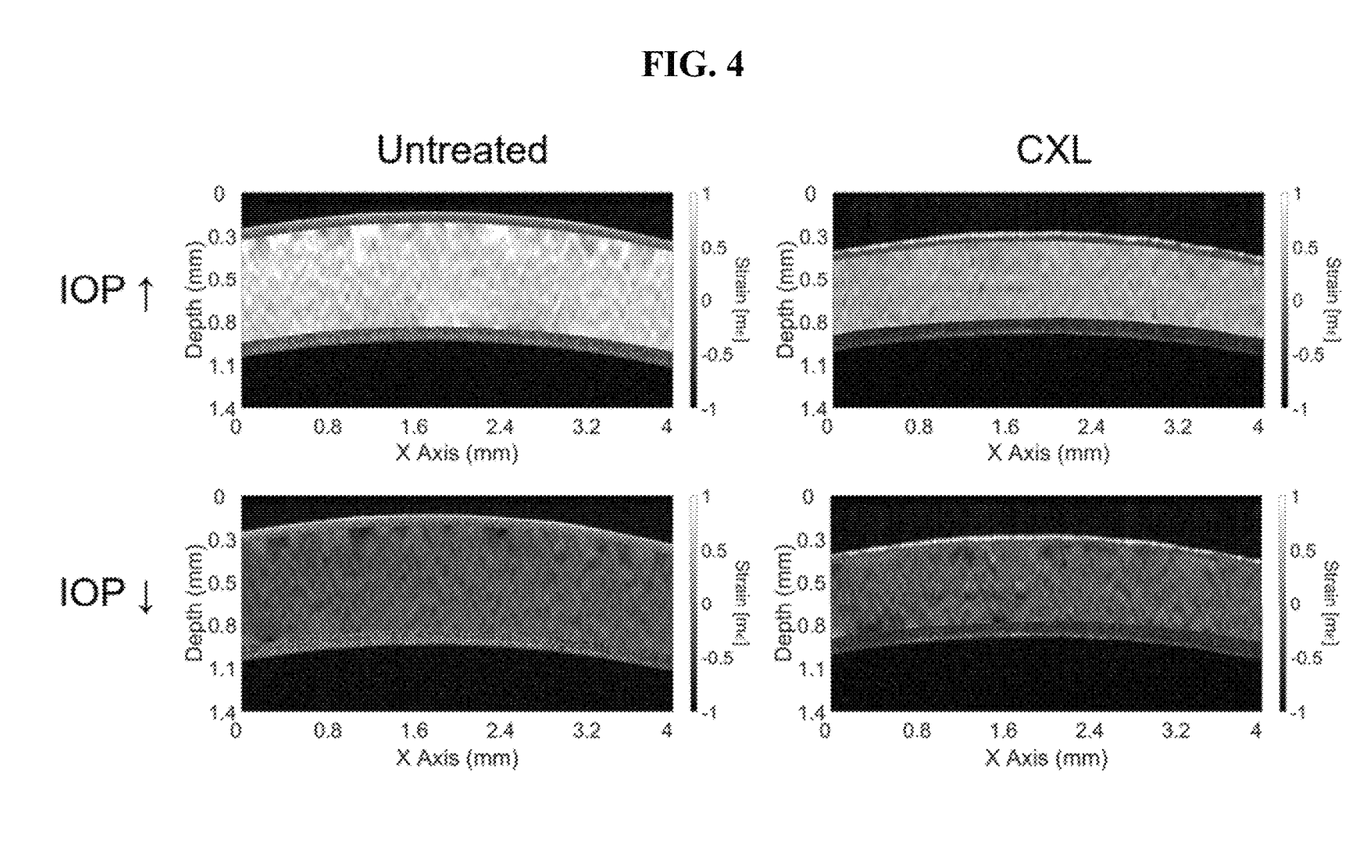
FIG. 4 shows (top left) strain in an untreated in situ porcine cornea where fluid is infused into the eye-globe to simulate one phase of the pulsatile motion in the cornea, (bottom left) strain in an untreated in situ porcine cornea where fluid is withdrawn from the eye-globe to simulate one phase of the pulsatile motion in the cornea, (top right) strain in an UV/riboflavin crosslinked in situ porcine cornea where fluid is infused into the eye-globe to simulate one phase of the pulsatile motion in the cornea, (bottom right) strain in an UV/riboflavin crosslinked in situ porcine cornea where fluid is withdrawn from the eye-globe to simulate one phase of the pulsatile motion in the cornea.

FIG. 4 shows the strain as calculated from FIG. 3. There is a positive strain (i.e., compression of the tissue) when fluid is infused into the eye-globe as seen in the top row of FIG. 4. On the other hand, there is a negative strain (i.e., expansion in the tissue) when fluid is withdrawn from the eye-globe as seen in the bottom row of FIG. 4. Crosslinking (CXL) reduces the magnitude of the strain, as seen when comparing the right column to the left column in FIG. 4, indicating that there was an increase in stiffness after CXL.

Figure 5:
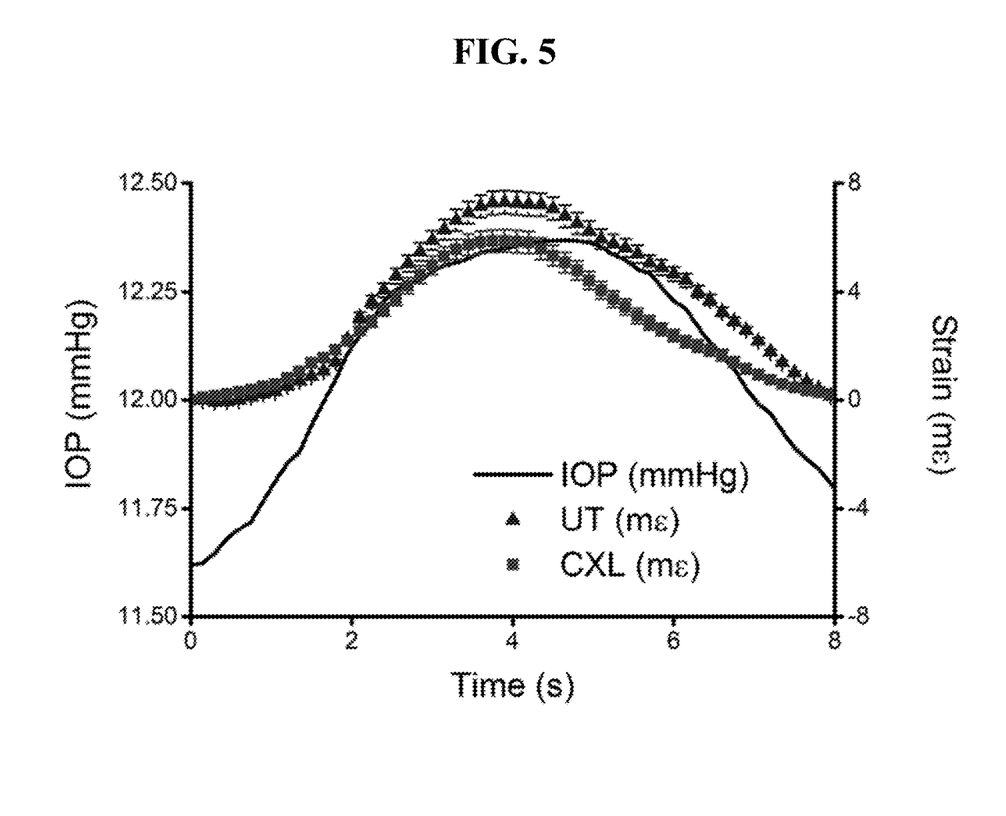
FIG. 5 shows the strain in an in situ porcine cornea (triangle) before (UT) and (square) after UV/riboflavin crosslinking (CXL) plotted alongside the intraocular pressure (IOP) of the eye-globe.

FIG. 5 shows a summary over one pulsation cycle showing the average strain across the cornea for the untreated (UT, triangle) and CXL (square) cornea as a function of the intraocular pressure (IOP) within the eye-globe. The points are the mean values and the error bars are the standard deviation.

Figure 6:
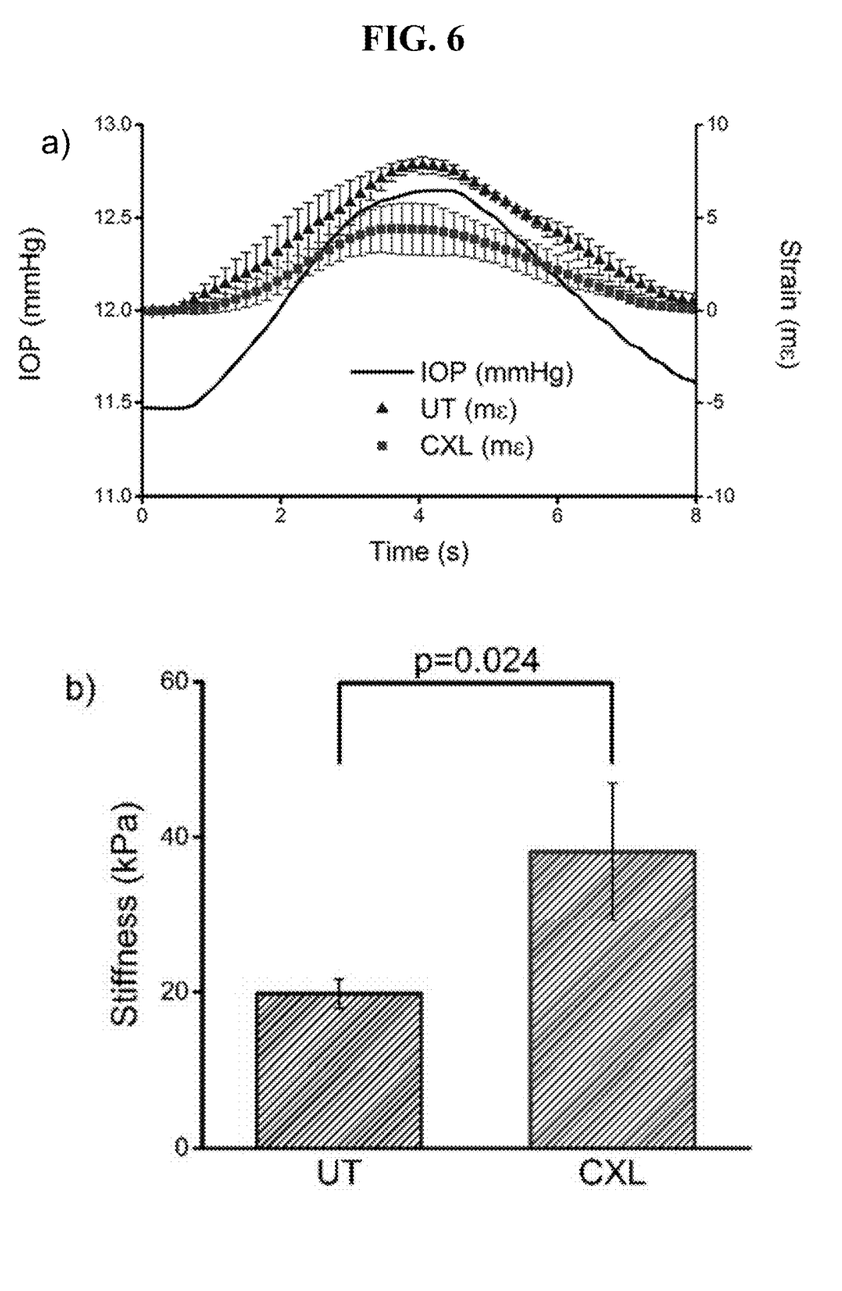
FIG. 6 shows (a) plots of the average and standard deviation of 3 in situ porcine corneas (triangle) before (UT) and (square) after (CXL) UV/riboflavin crosslinking plotted alongside the (solid line) eye-globe intraocular pressure (IOP) and (b) stiffness of the porcine corneas (UT) before and (CXL) after UV/riboflavin crosslinking with the p-value of the two sample t-test indicated.

The experiments were repeated on 3 corneas. FIG. 6(a) shows the (points) average and (error bars) standard deviation of the strain in 3 porcine corneas before (UT, triangle) and after CXL (squares) as a function of IOP. FIG. 6(b) shows that there was a statistical difference between the stiffness of the porcine corneas (UT) before and (CXL) after UV/riboflavin crosslinking with the p-value of the two sample t-test indicated.

Figure 7:
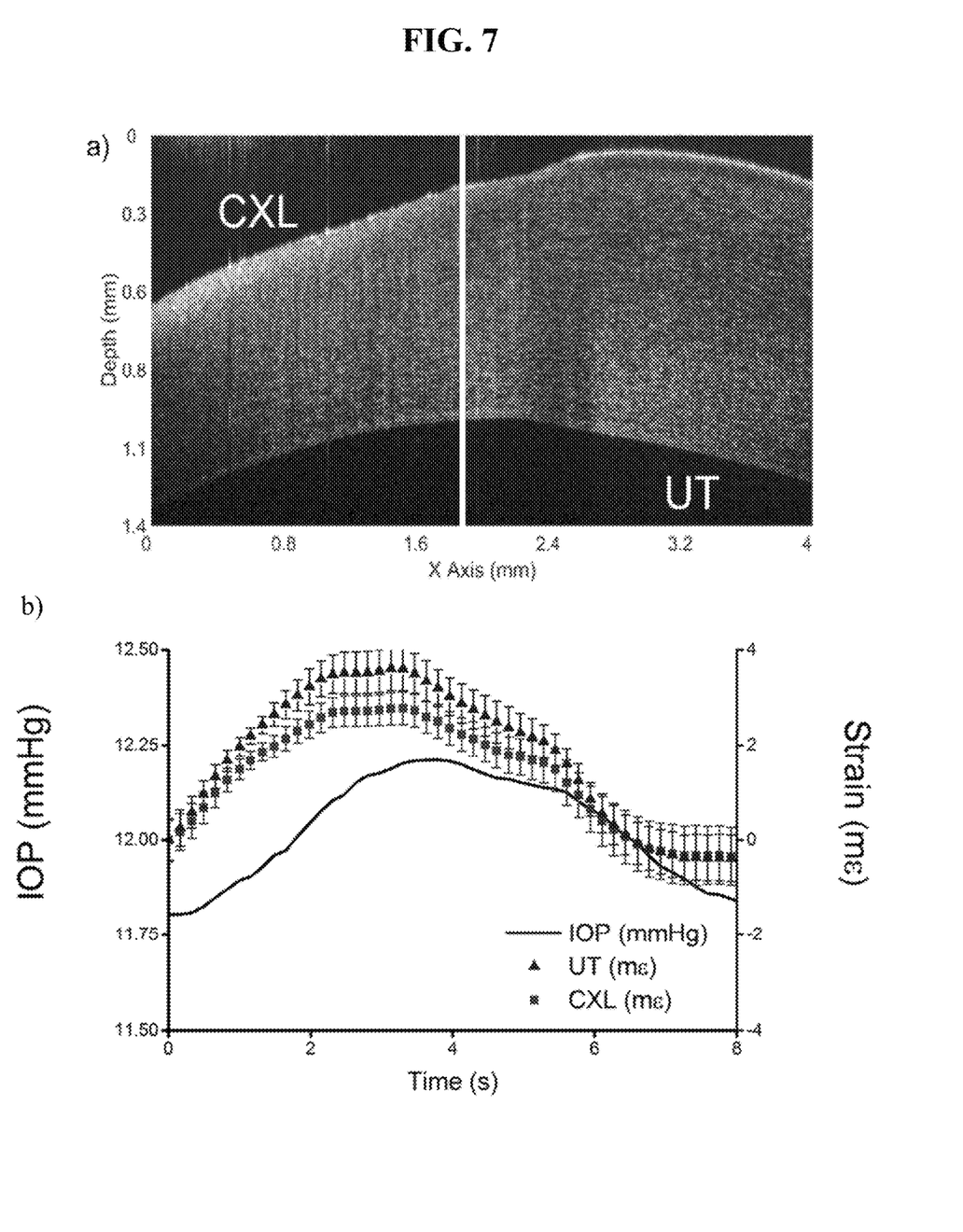
FIG. 7 shows (a) a structural OCT image of a partially UV/riboflavin crosslinked in situ porcine cornea where the left side was crosslinked (CXL) and the right side was untreated (UT) and (b) the localized strain in both regions (triangle—untreated; square—CXL) plotted alongside the (solid line) intraocular pressure (IOP) within the eye-globe.

Additional validation was performed on a partially CXL porcine cornea in situ. Here the same "Dresden" CXL protocol was performed on the cornea, except half of the cornea was covered to prevent any incident ultraviolet illumination, thereby preventing any crosslinking. FIG. 7(a) shows an OCT structural image where the left side was CXL and the right side was untreated (UT). FIG. 7(b) shows the strain as a function of the eye-globe intraocular pressure (IOP) for the untreated (UT, triangle) and CXL (square) regions of the cornea. The points are the average strain, and the error bars are the standard deviation.

Example 2. In Vivo Corneal Stiffness

To validate the ability of the system and algorithms to measure the pulsatile motion in the cornea in vivo, experiments were carried out in a live rabbit model. The animals were anesthetized with an approved dose and monitored by trained and certified veterinarians. A pressure transducer was mounted to the chest of the animal for corroboration with the OCE measurements. A glass slide was mounted to the OCE system, and the rabbit cornea was lightly compressed against the glass slide for stabilization. The same methodology, as outlined in FIG. 2 was utilized.

Figures 8A, 8B:
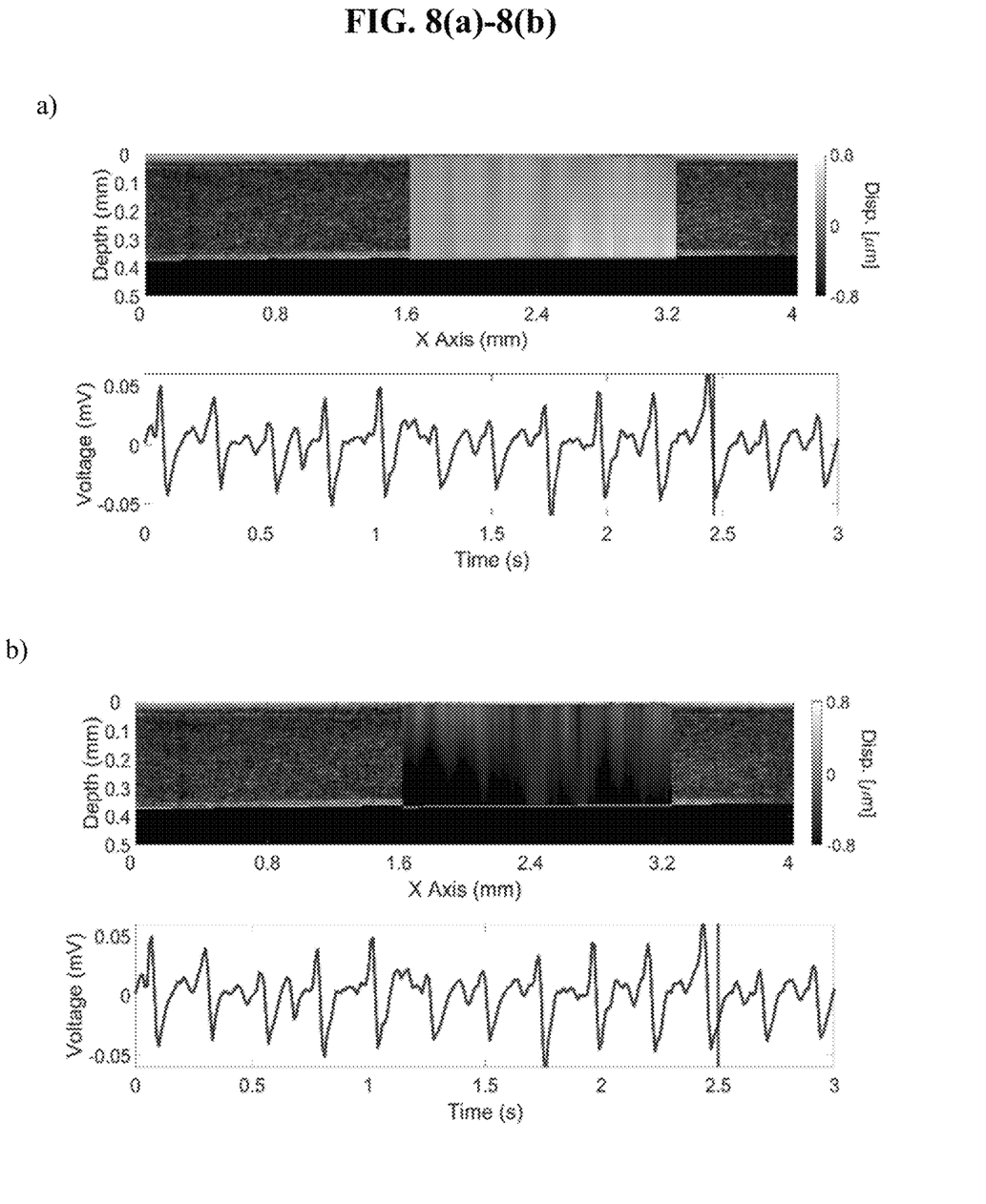
Figure 8C:
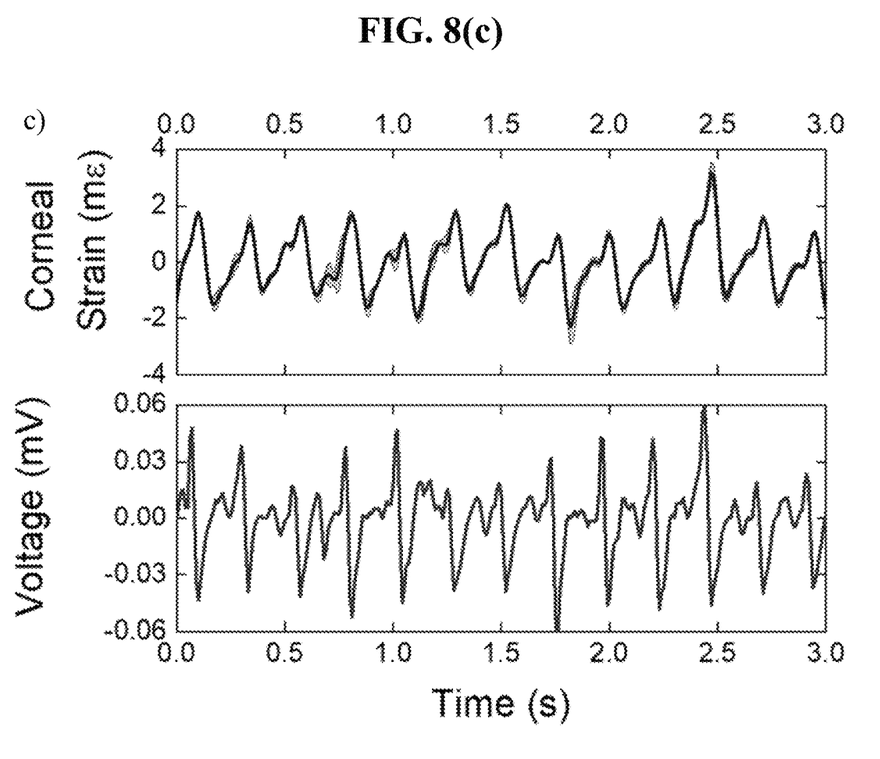

FIGS. 8 (a) and (b) show two sample differential displacement frames (i.e., change in displacement from the previous frame) plotted as a function of the voltage from the chest-mounted pressure transducer. The voltage corresponding to the frame is indicated by the vertical line in the voltage plot. FIG. 8 (c) shows the average (solid line) and standard deviation (shaded region) of the strain in the cornea, which is plotted alongside the voltage of the chest-mounted pressure transducer. The results show the system and method can detect the pulsatile motion in the cornea due to the heartbeat.

Figure 9:
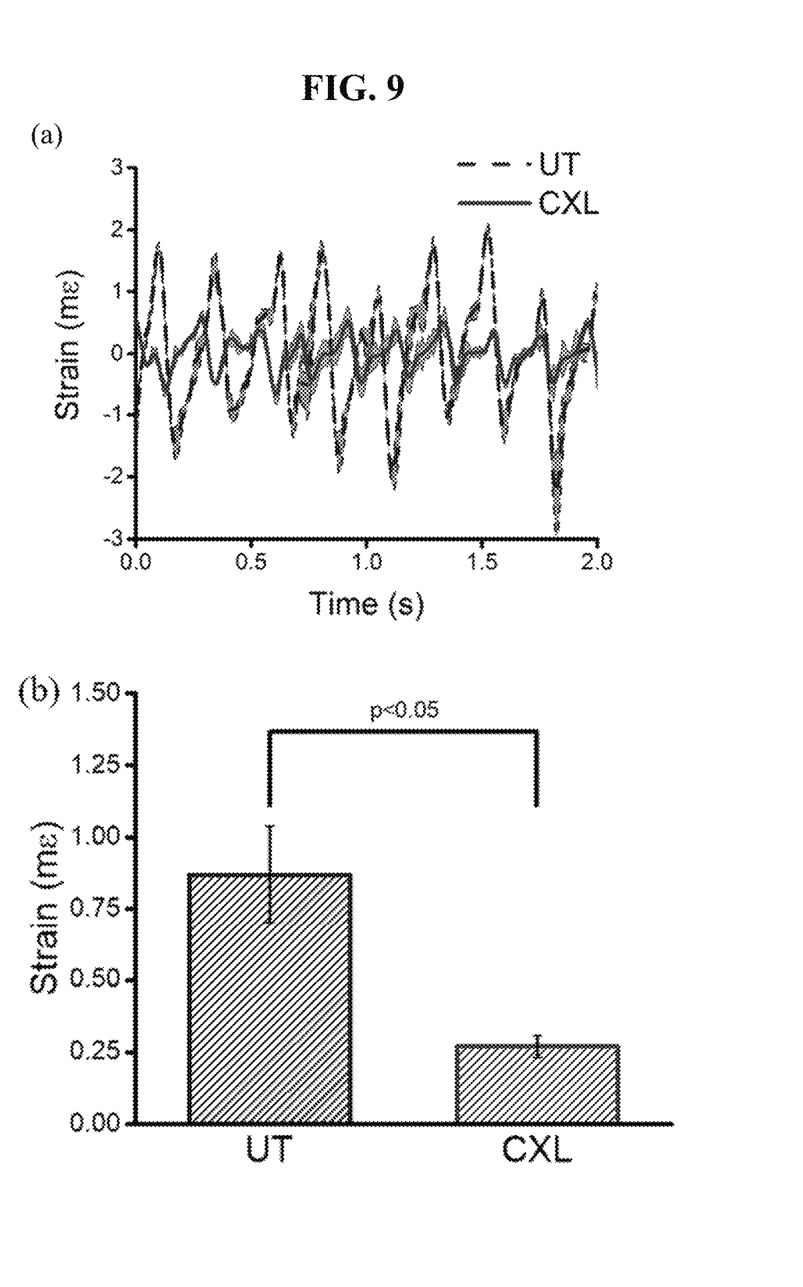
FIG. 9 shows (a) the (line) average and (shaded region) standard deviation of the strain in a rabbit cornea in vivo (UT, dashed line) before and (CXL, solid line) after riboflavin/UV crosslinking and (b) strain after crosslinking, indicating a significant increase in stiffness.

FIG. 9 (a) shows the results of the strain in the rabbit cornea in vivo before (UT, dashed line) and after (CXL, solid line) riboflavin/UV crosslinking. The lines are the regional average and the shaded region is the standard deviation. There was a statistical difference in the strain after CXL as shown in FIG. 9 (b), indicating a significant increase in stiffness.

What is claimed is:

1. A method for measuring biomechanical properties of a tissue sample in a subject without external excitation using optical coherence elastography, comprising:
   producing images of one or more regions of the tissue sample using phase sensitive low coherence interferometry or optical coherence tomography;
   detecting motion of the one or more regions of the tissue sample in the images, wherein at least a portion of the motion is caused by an internal force in the subject;
   correcting the motion detected to remove motion caused by forces other than the internal force, to produce detected intrinsic motion in images of the tissue sample;
   determining motion information between images of the tissue sample showing detected intrinsic motion; and
   calculating biomechanical properties of regions of the tissue sample using the motion information.

2. The method of claim 1, wherein the tissue sample is ocular tissue.

3. The method of claim 1, wherein the images of the one or more regions of the tissue sample are produced in 2D, 3D, or 4D.

4. The method of claim 1, wherein the images of the one or more regions of the tissue sample are produced using optical coherence tomography.

5. The method of claim 1, wherein the biomechanical properties comprise displacement, strain, elasticity, bulk modulus, Young's modulus, and combinations thereof.

6. The method of claim 5, wherein the biomechanical properties comprise displacement, wherein the displacement is calculated using phase-sensitive measurements, speckle tracking, motion tracking, or digital correlation methods, and wherein the displacement is in any direction.

7. The method of claim 1, wherein the internal force is pulsatile motion in the subject induced by physiological processes.

8. The method of claim 7, where the pulsatile motion is created by a heartbeat.

9. The method of claim 1, further comprising the step of differentiating regions of the tissue samples having different biomechanical properties.

* * * * *

UNITED STATES PATENT AND TRADEMARK OFFICE
CERTIFICATE OF CORRECTION

PATENT NO. : 11,406,258 B2
APPLICATION NO. : 16/907424
DATED : August 9, 2022
INVENTOR(S) : Kirill V. Larin et al.

It is certified that error appears in the above-identified patent and that said Letters Patent is hereby corrected as shown below:

In the Specification

1. In Column 5, Line 60, delete "α," and insert -- σ, --, therefor.

Signed and Sealed this
Fifteenth Day of November, 2022

Katherine Kelly Vidal
*Director of the United States Patent and Trademark Office*